(12) United States Patent
Goldstein et al.

(10) Patent No.: US 6,429,019 B1
(45) Date of Patent: Aug. 6, 2002

(54) CARBON MONOXIDE DETECTION AND PURIFICATION SYSTEM FOR FUELS CELLS

(75) Inventors: Mark K. Goldstein, Del Mar; Jaeseok Ryu, San Diego; Gerhard N. Schrauzer, Coronado; Lucian Scripca, San Diego, all of CA (US)

(73) Assignee: Quantum Group, Inc., San Diego, CA (US)

(*) Notice: Subject to any disclaimer, the term of this patent is extended or adjusted under 35 U.S.C. 154(b) by 0 days.

(21) Appl. No.: 09/487,512

(22) Filed: Jan. 19, 2000

Related U.S. Application Data

(60) Provisional application No. 60/116,323, filed on Jan. 19, 1999.

(51) Int. Cl.[7] .............................................. G01N 33/00
(52) U.S. Cl. ...................... 436/134; 436/167; 422/86; 422/93; 422/111
(58) Field of Search ............................ 422/86, 87, 90, 422/93, 110, 111, 119; 436/134, 164, 167

(56) References Cited

U.S. PATENT DOCUMENTS

| | | | |
|---|---|---|---|
| 4,012,692 A | * 3/1977 | Eicker ......................... 324/71.1 |
| 4,030,887 A | * 6/1977 | Poli et al. | |
| 4,043,934 A | 8/1977 | Shuler et al. ................. 252/186 |
| 5,063,164 A | 11/1991 | Goldstein ..................... 436/169 |
| 5,280,273 A | 1/1994 | Goldstein ..................... 340/632 |
| 5,302,350 A | 4/1994 | Goswami et al. .............. 422/86 |
| 5,346,671 A | 9/1994 | Goswami et al. .............. 422/86 |
| 5,388,405 A | * 2/1995 | Fujishita et al. .............. 422/169 |
| 5,405,583 A | 4/1995 | Goswami et al. .............. 422/86 |
| 5,573,953 A | 11/1996 | Marnie et al. ................ 436/164 |
| 5,618,493 A | 4/1997 | Goldstein et al. ............. 422/57 |
| 5,624,848 A | 4/1997 | Marnie et al. ................ 436/164 |
| 5,662,737 A | 9/1997 | Chen ......................... 106/287.18 |
| 5,793,295 A | 8/1998 | Goldstein ..................... 340/632 |
| 5,985,673 A | * 11/1999 | Bao et al. .................... 204/431 |
| 6,245,214 B1 | * 9/2001 | Rehg et al. .................. 205/763 |

* cited by examiner

Primary Examiner—Jeffrey Snay
(74) Attorney, Agent, or Firm—Christie, Parker & Hale, LLP

(57) ABSTRACT

The present invention provides an apparatus and method for determining the concentration of CO gas in a fuel reformate stream such as in a PEM fuel cell vehicle. This invention protects the fuel cell catalyst by controlling the reformate stream system to minimize the CO and reduce it by a novel catalyst system that selectively converts CO to methane but does not react with carbon dioxide and hydrogen. The catalyst may reduce the CO to methane by reaction with hydrogen. The preferred embodiment both monitors the CO by a thermal differential sensing means and an optical biomimetic sensor and or a conductivity sensor. These sensors respond to the CO gas and are monitored by one or more monitoring sensors such as the temperature and or conductivity difference between the control and the catalytic material such as nickel and in the biomimetic sensor an optical change is monitored. The optical sensing comprising a photon source optically coupled to the sensor and photodiode system, so that the photon flux is a function of at least one other sensor's response to the CO gas, e.g., transmits light through the sensor to the photodiode. The photocurrent from the photodiode is converted to a digital sensor reading value proportional to the optical characteristic(s) of the sensor(s) as a function of time and the data is loaded into a microprocessor or other logic circuit. In the microprocessor, the sensor readings are essentially used to calculate the CO concentration and control the process to maximize the fuel cell or to trigger a signal for service.

29 Claims, 8 Drawing Sheets

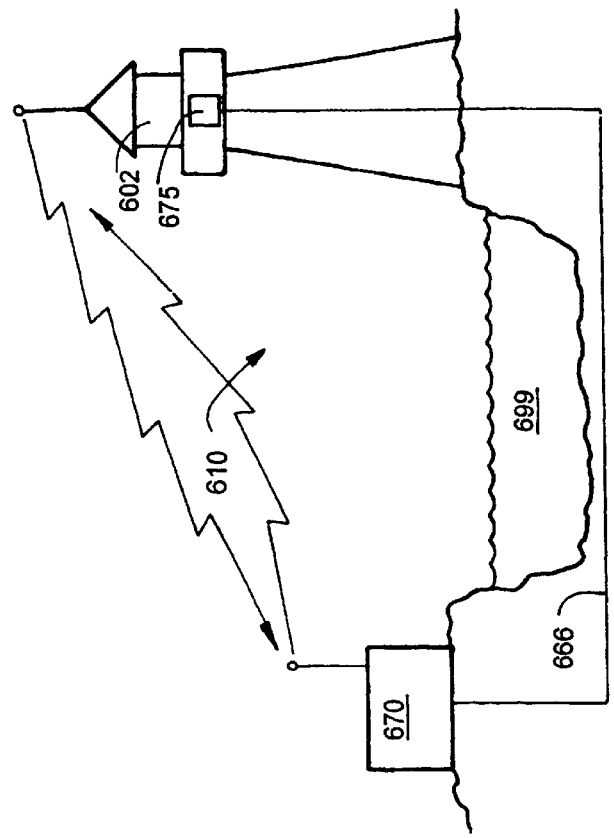
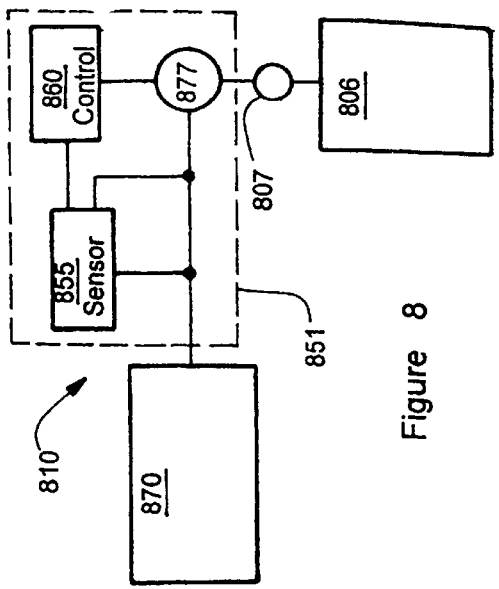
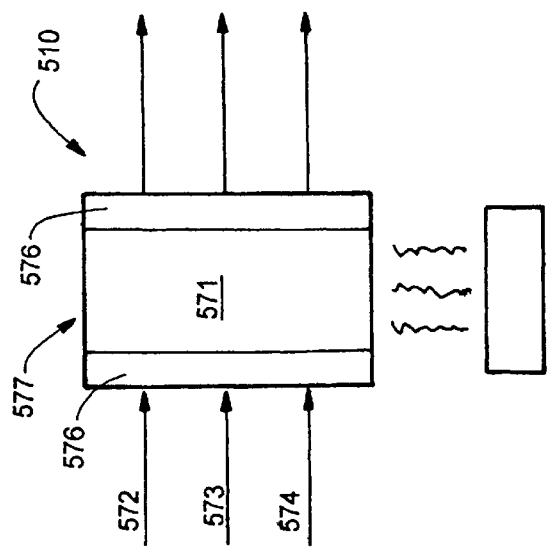
Figure 5
Figure 6
Figure 7
Figure 8

CARBON MONOXIDE DETECTION AND PURIFICATION SYSTEM FOR FUELS CELLS

RELATION TO COPENDING PATENT APPLICATION

This application claims benefit of U.S. Provisional Patent Application Serial No. 60/116,323 filed on Jan. 19, 1999, which application is incorporated herein by reference.

FIELD OF THE INVENTION

The present invention relates to a system used detect and remove carbon monoxide from a hydrogen rich stream in a fuel cell to thereby protect and optimize the service life of a fuel cell catalyst.

BACKGROUND OF THE INVENTION

In the 1960s, fuel cells were used in spacecraft during the Gemini and Apollo programs. Since that time various governments and industry have pumped billions into the development of fuel cells, because of their potential advantages. These advantages include environmental, stealth, efficiency as well as simplicity. In the 1980s General Motors concluded that the proton-exchange membrane (PEM) was well suited to vehicle applications. Fuel cells covert hydrogen and oxygen to water without the need for combustion. The process takes place at a much higher efficiency than heat engines. The theoretical efficiency is about 83% ("Fuel Cell" Energy Handbook, DOE/IR/05114-1) Oak Ridge; Tenn. June 1982 pages 136 to 144 by S. Glasstone. The PEM operates at about 80 to 90° C., which makes its platinum-based catalyst extremely sensitive to carbon monoxide (CO) poisoning.

CO bonds to platinum more aggressively than hydrogen, causing the power density to be greatly reduced. However, pure hydrogen can restore the catalyst. Therefore, it is very important to accurately sense the CO levels within a fuel cell and reduce the CO level during its operation. Similar problems occur in other applications of PEM-type fuel cells as well as other chemical process, which use hydrogen with a catalyst such as ammonia production.

The CO danger associated with gasoline-powered, internal combustion vehicles is well known, as over 1,000 people lose their lives annually due to vehicle generated CO according to the Mayo Clinic. In addition, according to the National Highway and Safety Administration, over 100 people lose their lives annually as a result of CO while the vehicle is moving. In view of these facts, CO sensors and detectors have been developed for gasoline-powered internal combustion engines. Goldstein has a co-pending application describes a means to provide safety to vehicle occupants from CO. In addition, examples of CO sensing means were described by Goldstein and by Goldstein et al, in the form of biomimetic sensors, in U.S. Pat. Nos. 5,063,164 and 5,618,493, which are incorporated herein by reference. The biomimetic sensors disclosed in these patents mimic the human response to CO.

The associated chemistry of palladium, molybdenum and copper were first described by Shuler and Schrauzer, i.e., in U.S. Pat. No. 4,043,934. This mixture was short lived and did not work over a wide range of temperature and humidity conditions as required by current standards. Therefore, advances were made using an organic material with supramolecular properties to stabilize and increase performance. In addition to chemical stability and performance superiority, U.S. Pat. No. 5,063,164 teaches that the presence of a target gas such as CO may be determined by monitoring the sensor with a photon source, i.e., by passing photons of a specific spectral region though the sensor and monitoring the intensity of the photon beam, or by using a pulsed photon source to conserve power with a simple photon detector such as a photodiode. There are a number of other target gas sensors that have been disclosed in the U.S. Pat. Nos. 4,043,934; 5,346,671; 5,405,583; 5,618,493; and 5,302,350, which can detect a target gas such as CO by monitoring the optical properties of the sensor.

Goldstein described several CO detector systems which incorporate this type of optical changing sensors such as the biomimetic sensor as discussed above such as in U.S. Pat. Nos. 5,280,273; 5,793,295, and others such as by Marnie et al that disclose a low cost circuit (Apparatus) with software and method for detecting CO in U.S. Pat. Nos. 5,573,953 and 5,624,848. Goldstein et al further disclosed a digital and rapid regenerating means in co-pending patent applications No. 60/051,038, Ser. No. 80/026,34 and No. 60/076,822 herein incorporated by reference. The gas detector systems include a housing containing photon sources that emit photons in at least a region of the electromagnetic spectrum that the sensor absorbs in response to the CO exposure, and a photodetector sensitive in the corresponding active region of the spectra, a circuit designed to measure the response, and a noise maker or other signal means which are actuated by the circuit and an enclosure. The housing (enclosure) has at least one opening to permit the sound to escape and the CO or other gas to enter. The detector also contains a sensor may be permanent or may be configured with a battery for convenient replacement or may be mounted within the housing designed for easy replacement and with or without a convenient battery replacement means. Several such systems were disclosed in U.S. Pat. No. 5,793,295, which is incorporated herein by reference.

In is, therefore, desired that a CO detection system be constructed for use with a fuel cell to detect and monitor the level of Co within the fuel cell. It is desired that such CO detection system comprise means for additionally controlling the CO level within the cell to protect a CO sensitive catalyst within the cell from CO poisoning. It is further desired that CO detection systems of this invention be capable of providing a signal output that can be used to warn a vehicle driver or occupant that the detected and monitored CO level be above a predetermined level.

SUMMARY OF THE INVENTION

There is provided several preferred embodiments of the present invention depending on the application, i.e., an apparatus and method for determining the concentration of any particular CO in a fuel cell hydrogen rich reformer stream. These CO detection systems are used as a control means for a fuel cell reform system including optimizing the reformer operation and secondary and tertiary CO removal systems.

Another important embodiment of this invention is incorporated into both fixed and portable reformer/fuel cell systems, and comprises basic sensor and circuit/software system. A built-in CO safety system can be used to control CO in the reforming process by adjusting various variables including flow, water, air, temperature, pressure and others. If problems with CO occurs, a light on the dash may be actuated as an indicator. For example, if the level of CO increases above a predetermined level, the light can flash or even display the level of hazard by digital or bar graph, or in word by vision or/or voice sounds. Further danger can result in louder warnings which may eventually shut down the fuel system supply to the fuel cell if it is not checked or serviced within a predetermined time period.

One aspect of a biomimetic sensor is that it regenerates in air. Therefore, a multiple sensor system is used with at least one sensor in the air stream and one in the hydrogen stream. A circuit means and microprocessor is used to measure the rate of change and the percent transmission of the sensor. A control means is used to modify the operation of the reformer and associated system to minimize the CO and maximize the efficiency of the fuel cell operation.

One preferred embodiment involves the use of a very low-power technology that also has a long service life, is fail safe, and will operate within a temperature range of from $-40°$ C. to $70°$ C. The technology is entitled "Solid State Infrared Reservoir" (SIR), and is the subject of a copending application No. 60/051,038 filed Jun. 27, 1998, which uses a sensor that responds to CO by a change in its optical properties for example as described in U.S. Pat. No. 5,063,164, and the improvement patents mentioned below in Example 1, and co-pending applications.

The sensor(s) of this system contain supramolecular complexes coated onto porous transparent elements whose optical properties change in response to CO under a variety of conditions, which can be optimized for specific application and temperatures.

An exemplary apparatus, according to the present invention, comprises a series of LEDs and photodiodes, with the target gas sensors located so that the photons emitted LEDs pass through the sensors and the amount of light transmitted is measured by the photodiode response to that light. Each LED illuminates a corresponding sensor, and the light transmitted through the sensor is received by the photodiode.

For a low-power, low-cost embodiment of the invention designed to determine the concentration of CO as the target gas, it is desirable to change the analog signal to digital (at very low power and low cost), the resulting photocurrent from the photodiode, proportional to the transmitted light received by the photodiode, charges a series of capacitors set to a threshold value programmed into the microprocessor as an action level such as an alarm point, this action level may also be further determine by the CO concentration.

In addition, it is useful to be able to turn on the catalytic converter within a closed environment when CO levels are above a predetermined level, e.g., 9 ppm. The alarm point can also be used to alert the driver about the need to service his vehicle, or alert a maintenance person about the need to provide maintenance to the reformer or components of the fuel cell system such as the hydrogen stream control system.

Several invention embodiments, including both apparatus and methodologies, are described in greater detail below with reference to the accompanying figures. In one preferred embodiment, a microprocessor is used to determine the points and time that the sensor readings are taken, and the alarm or some other action levels, and to store recent data of $I(n,t)$ and $dI/dt$ for the most sensitive sensors, which is in the linear region, and further to determine which equation or look up table to use within the microprocessor system.

One preferred low-cost method of monitoring the optical characteristics of a sensor is to determine the optical change at intervals of time (delta t) or ($\Delta t$) and place some of this data in a look up table for the case where the target gas is CO as has been described by Marine et al. in U.S. Pat. Nos. 5,573,973 and 5,624,848, incorporated herein by reference.

Preferred embodiments of this invention vary widely depending on the application, e.g., a detector may also be designed to display digitally the levels of CO, which is the subject of a co-pending application.

By this general method of operation, the level of sensed CO is determined by measuring the rate of change of light transmission through the sensor $dI/dt$ and $I(n,t)$ and then depending on that information action is trigger by the circuit.

BRIEF DESCRIPTION OF THE DRAWINGS

The invention will be better understood with reference to the following detailed description and accompanying drawings wherein:

FIG. 5 is a perspective view of one filter element of a reducing CO removal system that converts CO to methane;

FIG. 6 schematically illustrates a system of this invention comprising the of a reformer system some distance from a fuel cell, wherein a hydrogen transmission line is used to deliver hydrogen to a lighthouse and a telemetry system is used to control various reformer functions;

FIG. 7 is a schematic view of the CO detection and removal system used in any hydrogen rich stream, such as that used in an ammonia production factory;

FIG. 8 is a schematic view of a portable hydrogen bottling operation including low-power, light-weight CO sensor system, control circuit, reformer, compressor and subsequent CO removal means;

DETAILED DESCRIPTION OF THE INVENTION

Figure 1:
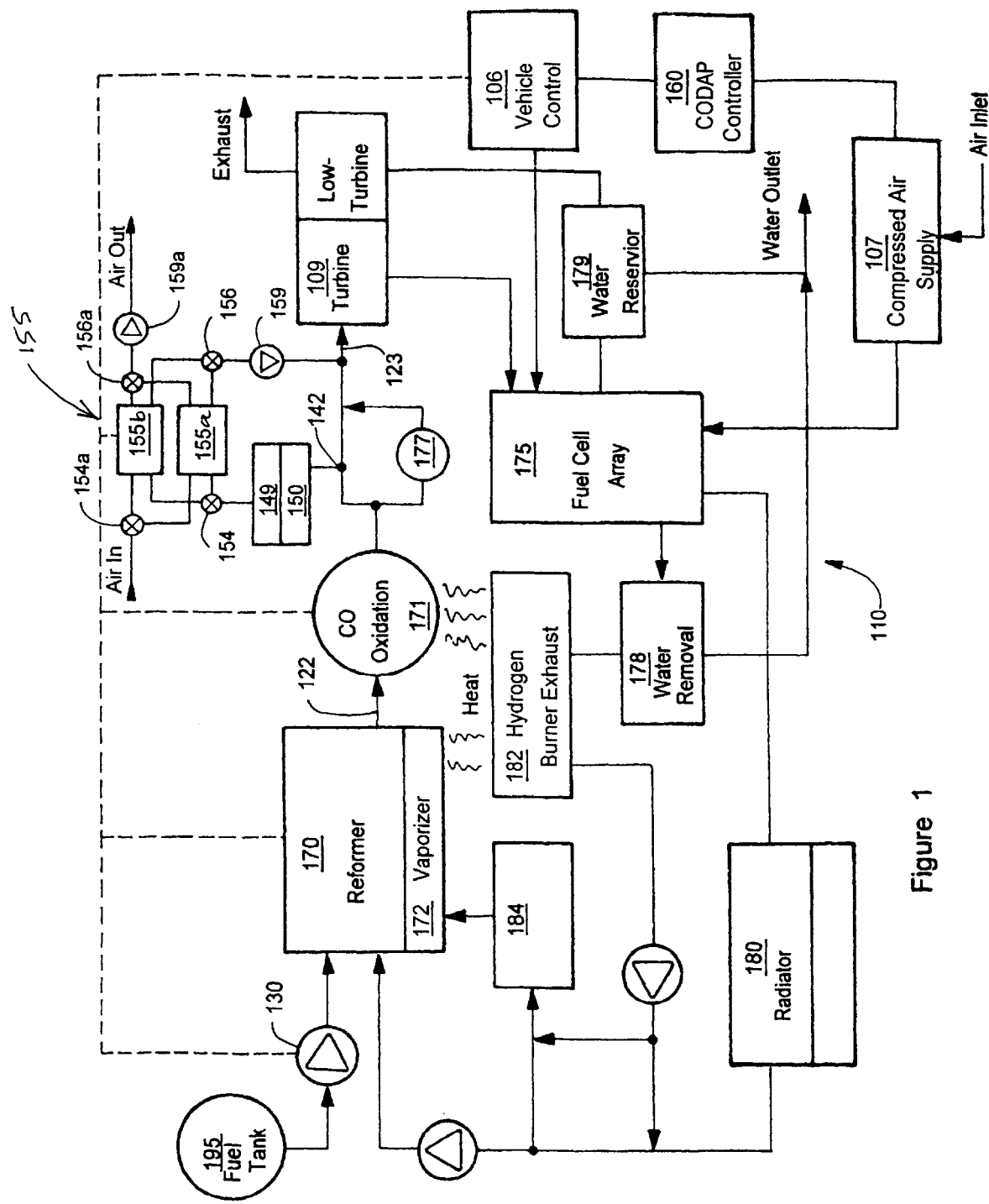
FIG. 1 is a schematic view of a fuel cell system including a reformer and CO detector apparatus attached between the reformer and the fuel cell stack.

An important use for the detection of CO in a hydrogen rich stream is in fuel cells, ammonia synthesis and other chemical processes. Of particular interest is the automotive fuel cell Carbon Monoxide Detection and Purification (CODAP) systems for use in reformate streams. CODAP systems need to be incorporated into most any fuel cell system that use a hydrocarbon reformer, e.g., currently vehicles under development by Mercedes Benz, Ford, General Motors and others. The sensing system needs to respond to CO from a few ppm to a few hundred ppm to protect the fuel cell catalyst (primarily platinum) and other catalyst for other chemical processes using hydrogen from becoming poisoned. Further, CODAP systems of this invention may include a means to reduce CO gas levels by changing operating parameters through a feedback circuit and/or by using a CO getter or catalytic reduction means such as converting CO to methane in a hydrogen stream with high hydrogen concentration and very low CO concentration.

Furthermore, CODAP systems of this invention may optionally warn the driver of a CO problem by audible, visual alerts to allow him time to get to a service station. In addition, the level of CO may be used to control the partial oxidation process step as well as other reformer process parameters. The presence of very high CO levels can endanger all occupants if there is a leak and, therefore, a CO device can also warn occupants of such a hazard. The warning may be visual and/or audible, and even shut off the fuel cell to protect people.

One type of CO sensor useful with this invention is biomimetic in nature, which requires oxygen for regeneration. This detector portion can be separated into at least two components; one sensing and the other regenerating at any given time. The biomimetic CO sensor can be used with an optical monitoring system, e.g., with an LED and photodiode.

A second type of CO sensor useful with this invention comprises two thermally-sensitive elements that respond to heat in a manner that is nearly identical in the absence of CO. One sensing element is coated with a catalyst and the other with a material with very similar thermal properties, but without catalytic activity. Assuming that the catalyst produces (or consumes) heat as result of a catalytic reaction with CO, then the amount of CO can be related to the differential heating in the two sensors. This thermal technique has advantages over the biomimetic sensor technique. For example, the thermally-sensitive sensor elements work at higher temperatures, require no valving for regeneration, and may be placed in the main fuel stream. The thermal method does, however, have some disadvantages, e.g., it does not work well when cold, it is difficult to locate both elements so they see identical flow, and calibration and operating range may be limited.

Therefore, it may be preferred in certain applications to use both types of sensing systems to assure proper reading during cold starts, and as early as possible to control the reformer system during rapidly changing conditions as well as providing a cross check on the time that sensing means needs servicing.

The sensor portion may contain a control system to provide feedback signals to the main control for the reformer process by varying temperature, air flow, fuel flow, etc. The CODAP system may add functions within the vehicle including operations of one or more catalytic convert purification systems to remove CO and a means to alert the driver of the need for service and shutting down the fuel cell system. One advantages of the catalytic sensor material that converts low levels of CO to methane in a hydrogen stream is that the same metal can be used in one of the CO removal means. The sensor degradation rate can be employed as an early indication of the need for service.

The CODAP system can detect and remove CO from the fuel cell reformer hydrogen rich stream. One or more of these CO detection devices may be incorporated into the vehicle or other fuel cell system in a way to optimize its service life and performance. This invention includes applications comprising one or more CO detector systems, a feedback means to reduce output of CO from the reformer system and CO removal system(s) as well as a signal means to alert the occupants in some way such as a visual or audible signal or both to prevent damage to the fuel cell should the control means fail to reduce CO below a certain level. Optionally, such device can display information on the concentration, compute and/or display the "Time to Next Service".

CODAP systems of this invention are understood to be used with a wide variety of fuel cells, such as passenger cars, trucks, boats, aircraft and other vehicles, ships, power plants and other applications where CO removal from gas streams is desirable. The gas detection device can be configured to send a signal to a means to control the CO emissions and or shut off the fuel cell system if all means to prevent CO to the catalyst fails, or just provide a audible and visual signal depending on the application.

One target of extreme importance to fuel cells is detection of CO from a methanol reformate, i.e., to accurately and reliably measure CO in the 1 to 1,000 ppm level range.

In addition, a control sensor was invented that responds to the environment in manner almost identical to a biomimetic sensor, except that no color change takes place in response to CO because the sensor contains a material that does not respond to CO.

The composition of one active CO sensor that has been shown to respond to CO in the presence of hydrogen was disclosed in U.S. Pat. No. 5,063,164, which is incorporated herein by reference. The concentration of copper may be higher than in normal air monitoring sensors, because the Pd ions transfer of electrons to molybdosilicic acid is revisable in air but not in hydrogen rich streams that contain no oxidizer such as oxygen.

The sensors will turn very dark upon exposure to CO and will undergo rapid regeneration upon exposure to air with CO levels below its threshold. The multiple sensor system and a few valves will allow the control of the system such that the sensor are always controlling and measuring CO in the hydrogen stream effectively. The two or more sensors are monitored photometrically, one in the hydrogen stream and at least one in the air. When the sensor in the stream nears saturation (color change takes place to an extreme) in response to CO, the valves are actuated. The valve actuation causes the second sensor to be exposed to the hydrogen rich gas stream and the first sensor to be exposed to air at about the same time. The invented system optionally includes a means to reduce the CO levels by one or more means, i.e., a catalyst whose composition resembles that of high surface area (rainy) nickel or nickel coated onto a high surface area porous substrate, either of which will convert CO to methane in a hydrogen rich environment. The information from the sensing system may be used to provide adjustments to the reform process and/or the partial oxidation catalytic reformer.

The biomimetic CO catalyst chemistry may be adjusted from the current composition for optimum performance. The chemistry is normally applied to a porous silica monolithic substrate by a self-assembly process. The porous silica monolith is coated with a supramolecular sensing material to form a sensing element. The reaction rate of CO with the sensing element is proportional to the CO concentration, and also depends on the relative humidity, temperature, pressure and oxygen. The sensing element is rapidly regenerated when exposed to clean air. Thus the alternating sensing and regenerating cycle allows smooth and efficient operation of the fuel cell system.

Another novel embodiment of this invention includes a CO removal filter with elements to remove the CO by means of conversion to methane using a metal catalyst. It has been known since 1928 that CO can be converted to methane (H. A. Bahr and T. A. Bahr Ber Dtch Chem Ges 61:2177 (1928). Recently, extensive research on synthetic fuels has lead to detailed studies of these types of methanation reactions over a nickel, palladium, cobalt and other metals see pages 110 to 129 in The Chemistry of "The Catalyzed Hydrogenation of Carbon Monoxide" by G. Henrici-Olive and S. Olive published by Springer Verlag (1984).

The CO removal system may include a nickel catalyst held in a gas filter system at about 200 to 300° C. such that the CO passing through Ni coated on a substrate (such as silica, titania or alumia) reacts the excess hydrogen to form methane. Heat may be applied to the catalyst or gas stream to increase the rate of conversion to methane.

In addition, some preferred embodiments of this CO sensor and control invention, places the sensor(s) on the vehicle or in a location between the reformer and the fuel cell stack. These types of CO sensing products may be operated on common batteries that can be easily replaced or they may be powered by the electric power from the fuel cell or its start up battery system. The sensor system may be replaced separately or with the battery. The most accurate detector system able to respond to less than 30 ppm CO contains sensor(s) that need to be replace every few years. A warning system that is calculated based on operating hours or sensor regeneration rate may be used to determine when the sensors need to be replaced.

In another case, the CO detection unit may contain a rechargeable battery, it may be recharged in the vehicles during operating or when used outside the vehicle. The rechargeable battery can act as battery back up in some applications, which is also advantageous. The device should be configured so that the back-up battery can be replaced safely by isolation of any possible line power from the vehicle or other source. This can be accomplished by means of an opening for the battery that requires the unit to be disconnecting from the power in order to get access to the battery or another isolation means. Certain vehicles such as electric cars powered by fuel cells are generally expected to include a hydrocarbon reformer to convert hydrocarbon to hydrogen, carbon dioxide and carbon monoxide. The CO sensing system may operate off of the main vehicle electric power generated by the fuel cell or other electric generation means and may also have a battery back up system. In addition, CO can be detected in some hybrid electric vehicles incorporating a fuel cell.

Any of the above CO detector technologies may be incorporated into the small size optically monitoring unit.

CO is often difficult to detect in a hydrogen stream operating within a temperature range of from about 200° C. to 300° C. Therefore, a small side-stream cooling means is provided for the sensor(s). In addition, a switching means is used to switch the flow from air to hydrogen for one or more sensors.

In one embodiment of the invention the switching system connects one sensor to the hydrogen stream while the other regenerates in an air stream. The process may be reversed as necessary. In addition, more than two sensors may be needed as shown below in the multiple sensor system.

The sensor system (including sensor-switching means) is operated by circuitry incorporated into the fuel cell containing vehicle, e.g., an automobile. In some cases, a dual or multiple sensor system may be used so that a spare sensor is always available if a sensor becomes saturated or otherwise fails to protect the expensive fuel cell from damage. This system will be described below in detail.

The sensor system may optionally be connected to an emergency catalyst or getter to remove CO from the stream should the normal system fail, giving the driver time to get to a service station.

EXAMPLE 1

Low-Power Sensing System

This example sets forth a low-power sensing system in a preferred low-cost embodiment of this invention for use with portable fuel cell applications such as those used with vehicles. The detection and control system incorporates one or more biomimetic sensor(s). These sensors consume no power; they monitored by optical means that take very little power. The control and monitoring systems used for detecting the presence of a predetermined concentration of a target gas, such as CO may take only a few microwatts. Several low-cost, low-powered biomimetic sensor systems are disclosed in U.S. Pat. Nos. 5,063,164; 5,624,848 (Marnie et al); U.S. Pat. No. 5,618,493, (Goldstein et al); U.S. Pat. No. 5,280,273 (Goldstein); U.S. Pat. No. 5,793,295 (Marnie et at) and higher-cost advanced systems are disclosed in co-pending patent application serial No. 60/076,822, filed Mar., 1998 and a digital CO detector PCT/US97/16846 Filed Sep., 19, 1997, the contents of which are incorporated herein by reference.

These sensor(s) comprise at a containing self-regenerating sensing reagent self-assembled onto a transparent high surface area substrate, for example, porous glass or porous silica. The substrate is made of a solid state material which is sufficiently transmissive to a specific range of photons in the specific wavelength region to interest to permit detection of optical characteristics of the sensor using an optical source such as a light emitting diode and a photodiode such as photodiode. These optical components and sensor(s) are controlled by a circuit designed to measure the output of the photodiode monitoring the sensor, which would control the reformer and CO conversion devices through some means and actuate controls as programmed depending on the CO level or other conditions.

These types of detectors can be modified to meet a variety of fuel cell requirements depending on the type of fuel being reformed. This may be accomplished by one of several software-hardware combinations described in U.S. Pat. Nos. 5,624,848 and 5,573,953 known as embodiment 1, incorporated herein by reference, and co-pending application using digital methodology described in PCT/US97/1686 known as embodiment 2, also incorporated herein by reference. Both embodiments 1 and 2 are preferred embodiments, the first for low cost and the second is preferred for performance features and accuracy, i.e., the high-end application.

A third embodiment is a modification of embodiment 1, e.g., based on di/dr Plus IK, where I is the intensity of photons and K is a constant. Under certain conditions, the derivative of the transmitted photon with respect to a time interval plus the actual transmitted photon Intensity is proportional to the CO concentration, $[CO] = k_1\{dI/dt\} + I(K_2)$ at other times $[CO] = k_2\{I(n)\}$ When dI/dt is very near zero And when dI/dt is not linear such that the second derivative is not very near zero, than the sum of the two, i.e., I(n) and dI/dt, is divided by 2 or an averaged or mean. In addition, a weighted average is feasible such as represented by the general equation:

[CO]=c{$k_1$[dI/dt]+$k_2$[I(n)]}

The approximation can be employed easily and can limit the cost of the alarm or detector and has the capability of digital display.

Other approximations are also possible, e.g., the sum of averages or weighted averages over a series of registers

[CO]=kl(dI/dt)+$K_2$[I(n)]

There are two basic optical techniques that can be incorporated as embodiments of the optical monitoring method: (1) transmission, as discussed above; and (2) reflection, a second embodiment of this invention.

Let us describe the transmissive method, as it is generally preferred. These methods can be used for a variety of gases for which a similar responding optical sensor exists. However, as an example, CO will be discussed as the target. By this exemplary focus on CO we in no way intend to limit the target gases of this method. This method may be useful in producing digital displaced CO concentrations.

Let discuss another possible feature of the invention that could apply to many embodiments, for example a sensor that changes its optical properties as a function of CO concentration and time such as a biomimetic or other optical responding sensor. In the absence of CO concentration the sensor does not change. In a gas stream without oxygen the sensor will not regenerate. Therefore, a means to periodically regenerate each sensor is required.

When the S34 sensor is place in relatively clean air (less than 30 ppm co), it will generated rapidly. The sensor chemistry may be adjusted to be the normal state under different than 30 ppm conditions. If a target gas such as CO is present above the threshold, the sensor equilibrium is shifted as the reagent undergoes changes in its optical density, i.e., the sensor begins to change its optical properties, e.g., it darkens or lightens depending on the particular environmental condition the age of the sensor, it saturation condition, the number of times it has been saturated, and various environmental conditions.

A Fifth embodiment of the invention employs the use of reflected photons to monitor the gas exposure and concentration of the CO gas. This method is similar to the one described above except that the photons are reflected off of the sensor(s) or from a reflector placed behind the sensor(s).

It is also possible to combine one or more of the above embodiments. The reflection off the surface of an optically changing sensor can be monitored by means of a LED and a photodetector. The light reflected from the surface change is proportional to the CO concentration and the time of exposure. The photons transmitted through the disk and reflected off of the mirror is transmitted twice through the sensor increasing sensitivity. Since in most cases some light is reflected off of the surface, this method tends to combine the transmission and reflection methods.

EXAMPLE 2

Thermally-Reactive CO Sensors

This example includes an active metal catalyst coated on the thermal responding means, e.g., a thermocouple or a thermistor. There may also be included a control sensor in the hydrogen rich stream that is closed to the catalytic sensor. Then the differential signal is directly related to the catalytic activity, which is proportional to the CO level in the stream. In an excess hydrogen stream, CO reacts with hydrogen to form methane. This same reaction can be used to remove small amounts of CO from the stream. The reaction creates a difference in the temperature of the two sensors. This sensing means has an advantage over the optically-reactive sensing means described above, as no regeneration step is needed.

A similar principle is used in a mass flow controller, e.g., the differential temperature measurement results from cooling the thermally-sensitive element relative to a control element. This temperature difference is related to a predetermined amount of flow on the sensor in the flow. In the same way, a differential temperature can be related to the CO concentration if the flow is known. If both the control sensing element and the catalytic coated sensor are near the center of a pipe equidistant from the walls, the flow pattern can be equivalent and thus cancel out all effects of flow and temperature within a specified range. Since the catalytic effects of nickel are preferred for this methane forming reaction, it is preferred to apply a high surface active nickel coating to one thermally sensitive element and a metal with a similar high surface area but little or no catalytic activity such as copper, gold, silver or an alloy of any mixture thereof.

Another method to measure CO in a hydrogen rich stream is to coat a thermistor with a very thin layer of porous silica or similar high surface area solid that does not conduct electricity. The substrate such as silica or alumina may be coated by means of a sol gel process. The typical process adds about 2 to 6 microns of porous material with a typical average pore diameter of about 20 angstroms. After the porous substrate is dried and fired, it is coated with a nearly monomolecular layer of metal catalyst such as nickel. The nickel reacts with the CO to form a nickel carbide which does not conduct electricity. The circuit sends a current through the catalyst surface and through a control sensor that does not react with CO but has a similar electrical conductivity. The differential conductivity is proportional to the CO concentration. The CO levels can be detected at very low levels with this method.

One skilled in the art may appreciate a light-weight, low-powered CO sensing control apparatus which can also measure and display digitally the gas concentration by calculations from the response of optically responding sensors for a variety of target gases. Today, our current digital gas detection products can not operate for years or even monthly with common batteries such as 9 volt alkaline or similar batteries, thus a rechargeable battery may be preferred. Such CO sensing and CO removing apparatus and method would increase the desirability of a wide variety of fuel cell products for home, industrial, commercial, military medical and automotive applications.

FIG. 1 illustrates a schematic view of a vehicle fuel cell system 110 comprising a small biomimetic CO detector system 155 of this invention for use in vehicle (not shown). The detector system 155 comprises two sensing units 155a and 155b that have a feed system through valve 142, which is used for sampling a hydrogen rich stream 122 from a reformer 170. The sampled stream is reduced in temperature by being passed through first a cooling means 150, through a membrane 149, and then though valve 154 to either sensing unit 155a or 155b. At least one of the sensors (not shown) in the sensing unit 155a or 155b comprises a porous silica disk coated with the biomimetic supramolecular sensing material. The fuel cell system comprises a main vehicle control block 106 that includes a circuit that operates the monitoring and control means 160.

The main vehicle control 106 is also connected to a fuel cell array 175, the fuel system reformer 170., a CO oxidation system 171, and a CO-to-methane emergency converter 177 in order to control and optimize the performance and efficiency in response to the driver and vehicle demands by monitoring CO and other parameters. The fuel (not shown) is contained in a fuel tank 195, which is pumped by a fuel pump feed 130 to the reformer 170 which comprises a vaporizer 172. The fuel is reformed, e.g., converted from methanol to hydrogen, carbon dioxide, and CO. The CO level produced by the reforming step is reduced by the selective oxidation (a shift reaction that coverts CO to carbon dioxide) in reactor 171. Heat may be supplied to the reactor 171 and to the vaporizer 172 by a hydrogen burner 182.

The hydrogen rich stream 122 exiting the reformer 170 is sampled by the valve 142, and a small fraction of the stream is cooled by the heat exchanger 150 with resulting condensed moisture being removed by the hydrophobic membrane 149. The fuel stream is then sensed for CO by sensors disposed within the in the sensing chambers or units 155a and 155b, and sample stream is returned to a fuel line 123. The fuel then passes through a turbine 109 to the fuel cell 175. Air is compressed by a compressor 107 and is directed to the opposite side of the cell array 175 and the two elements, i.e., oxygen and hydrogen, react electrochemically (not shown) to produce electrons and water. Water produced within the fuel cell array exits along the bottom to the reservoir 179 and 178 the water removal means. A radiator 180 cools the fuel cell system with water. The hydrogen burner 182 provides heat to the reformer 170 and reactor 171 at start up and during operation. A waste-heat recovery system 184 is also used to facilitate the heating process.

Figure 2:
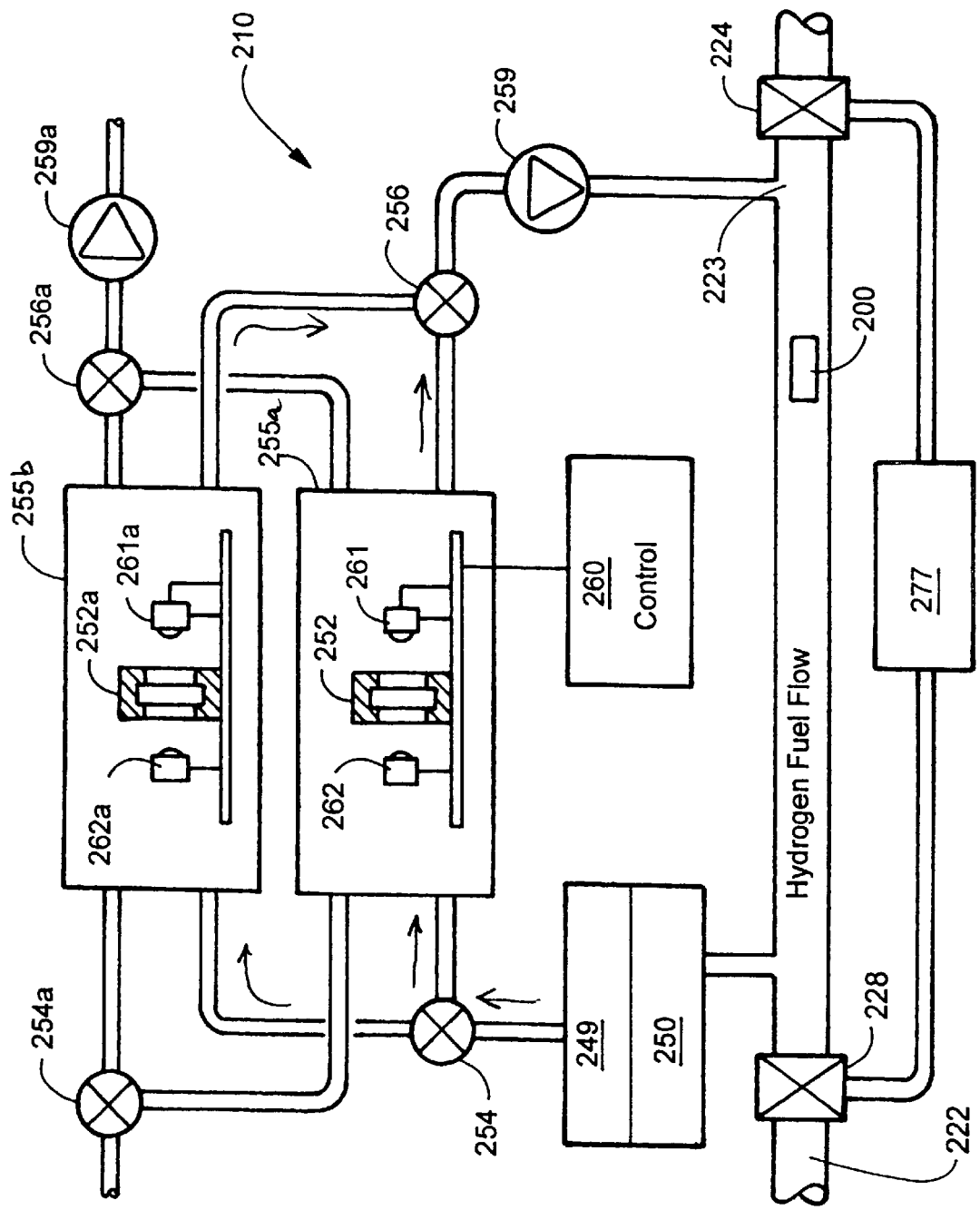
FIG. 2 is a schematic view of a dual CO detector system with a controller to operate regeneration and detection modes of the system.

FIG. 2 depicts a schematic view of the sensing system 210 provided in FIG. 1, and more clearly illustrates how the system is connected to the fuel cell hydrogen rich stream 222. The system 210 comprises two sensor chambers or units 255a and 255b, which each comprise one or two respective sensors 252 and 252a that are monitored by respective LEDs 261 and 261a, and respective photodiodes 262 and 262a. The fuel stream 222 from the reformer comprises hydrogen, carbon dioxide, nitrogen, water and a small amount of other gases including CO (not shown). A small amount of the fuel stream is diverted to one of the sensor chambers 255a and 255b. Each of the sensor chambers are configured having air flowing through them so that the sensor(s) within each chamber can regenerate. The hydrogen rich fuel stream is passed from the main fuel line 222 to the cooling heat exchanger 250, with any condensed moisture being removed by a membrane 249. The fuel stream then passes into one of the sensor chambers 255a or 255b where the CO within the stream reacts with the one or more sensor within the chamber, wherein the rate of that reaction is proportional to the CO concentration.

A control circuit 260 measures and determines the CO level and then adjusts the operation of the reformer (not shown) and selective oxidation process (not shown) to convert more CO to carbon dioxide, or use another means to reduce the CO levels such as catalytic reducer 277 to form methane. If the adjustment fails to reduce the CO level, the power will drop and the driver will be warned to seek immediate service of his vehicle. An emergency CO removal system 277, e.g., a catalytic reactor, may be used to allow the driver time to get to a service facility (not shown). The controller 260 may use valves 228 and 224 to direct the CO and hydrogen through the catalytic reactor 277 that converts CO and hydrogen to methane.

Figure 10:
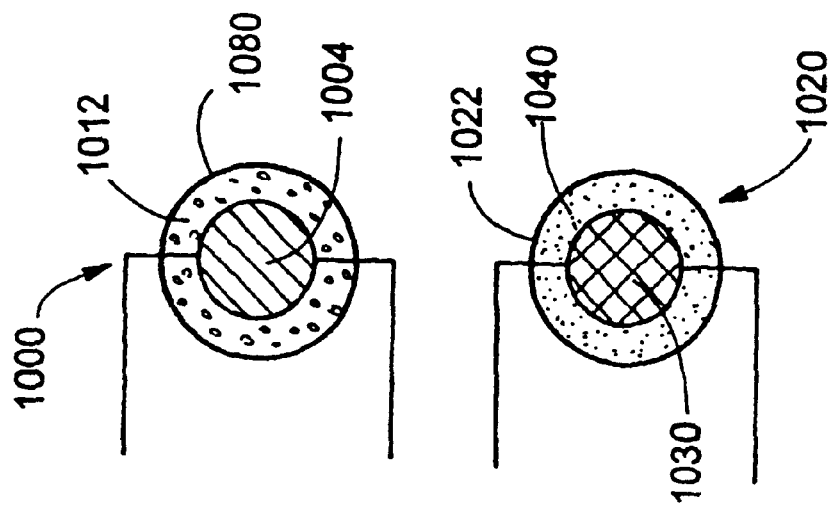
FIG. 10 schematically illustrates means used for preparing the differential catalytic sensor system for detection of CO in a reformate stream.

A portion of the hydrogen rich stream exits the sensing chamber through a valve 256 and then returns to the main fuel steam 222 at position 2233. As the sensor within the sensor chamber begins to saturate, the valve system 254 and 256 switches the flow of fuel from one sensor chamber 255a to the other 255b, and the air stream is switched valve system 254a and 256a from the fresh sensor chamber 255b to the saturated sensor chamber 255a. There is optionally another CO sensing device 200 that operates on the principal of differential temperature measurement as described in greater detail below and as illustrated in FIG. 10.

The sensor control 260 is needed to measure the CO concentration and control the CO sensors in 200, 255a, and 255b. The control 260 controls various valves 256 and 256a and pumps 259 and 259a which are important in the sensing and regeneration steps of the sensing operation. In addition, inlet control valves to the chambers 255a and 255b, such as 254 and 254a, control the respective hydrogen and air feed streams to the sensors 252 and 252a disposed therein. The control 260 provides signals to operate the reformer (not shown) through the vehicle control means (not shown) or directly. The system may use more than two sensor chambers, although to simplify explanation of the system operation only two are described herein.

A control sensor (not shown) may be used to correct for temperature, relative humidity, and component variations. Most of these variations can be canceled out by measuring the differences between sensor and control sensor elements, especially if the sensors are formed from the same batch of substrate and all the chemicals except palladium is used (platinum may be substituted for the palladium to make a control sensor). Alternately, the humidity, temperature and other parameters will be measured and the microprocessor can calculate the effects of these parameters on the CO concentration. The equation for interference can be developed by testing in various gas streams in the lab. The data can be fitted top an equation or a look up table may be employed.

Figure 3:
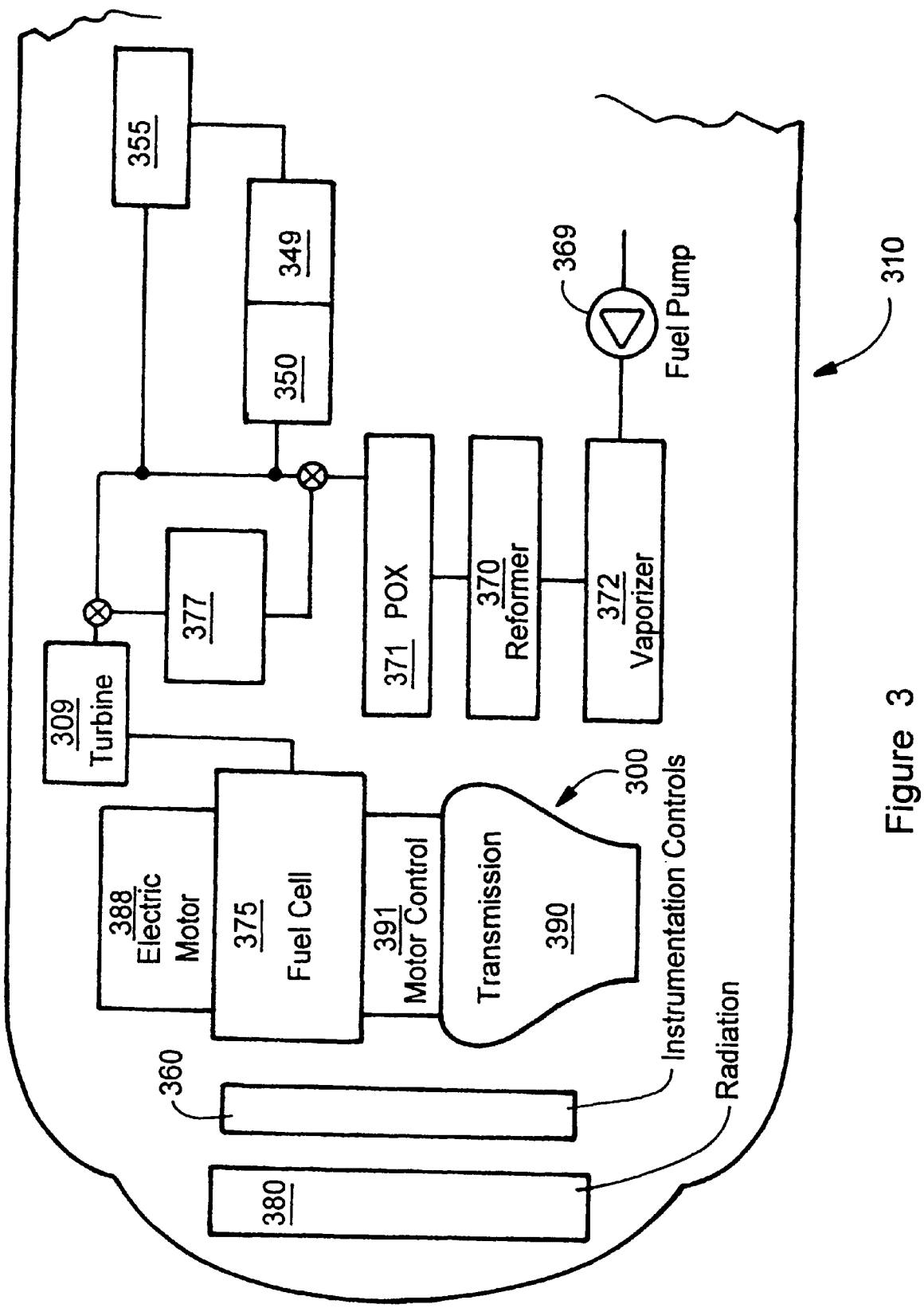
FIG. 3 is a front view cut away of an fuel cell powered vehicle with methanol reformer, fuel cell, electric motor, transmission, instrumentation unit, and a CO detector system of this invention.

FIG. 3 illustrates a top view of a hood of a typical fuel cell powered vehicle 310 for a passenger vehicle. At the front of the vehicle is the radiator 380, which remove excess heat from the fuel cell 375. The entire fuel cell system 300 is controlled by an instrumentation control 360. The fuel such as methanol is pumped by a fuel pump 369 to the vaporizer 372 which then enters the reformer system 370, which enters a catalyst section and other heat exchange means (not shown). The methanol is converted to hydrogen and carbon dioxide by a partial oxidation method, which adds moisture to the gas steam and small amount of CO. A portion of the stream shifts the reaction from CO to carbon dioxide in a catalytic oxidizer or reactor 371.

An outlet stream from the catalytic oxidizer or reactor 371 is routed to a CO sensor system of this invention based on thermal differential measurement using a nickel catalyst. A selected portion of the reactor outlet stream may be passed through a cooling means 350 and a hydrophobic membrane 349 before reaching a biomimetic sensor system 355 for measurement of the CO at 30° C. The stream may be directed through a CO removal stream 377 which converts the CO to methane to bring the stream down to less than a few ppm, CO, e.g., 1 ppm or less. The clean fuel is then passed through a fuel cell 375 where the energy of the fuel is converted directly to electricity, which drives a motor 388, which in turn is transferred to the vehicle via a motor control 391 and a transmission 390.

Figure 4:
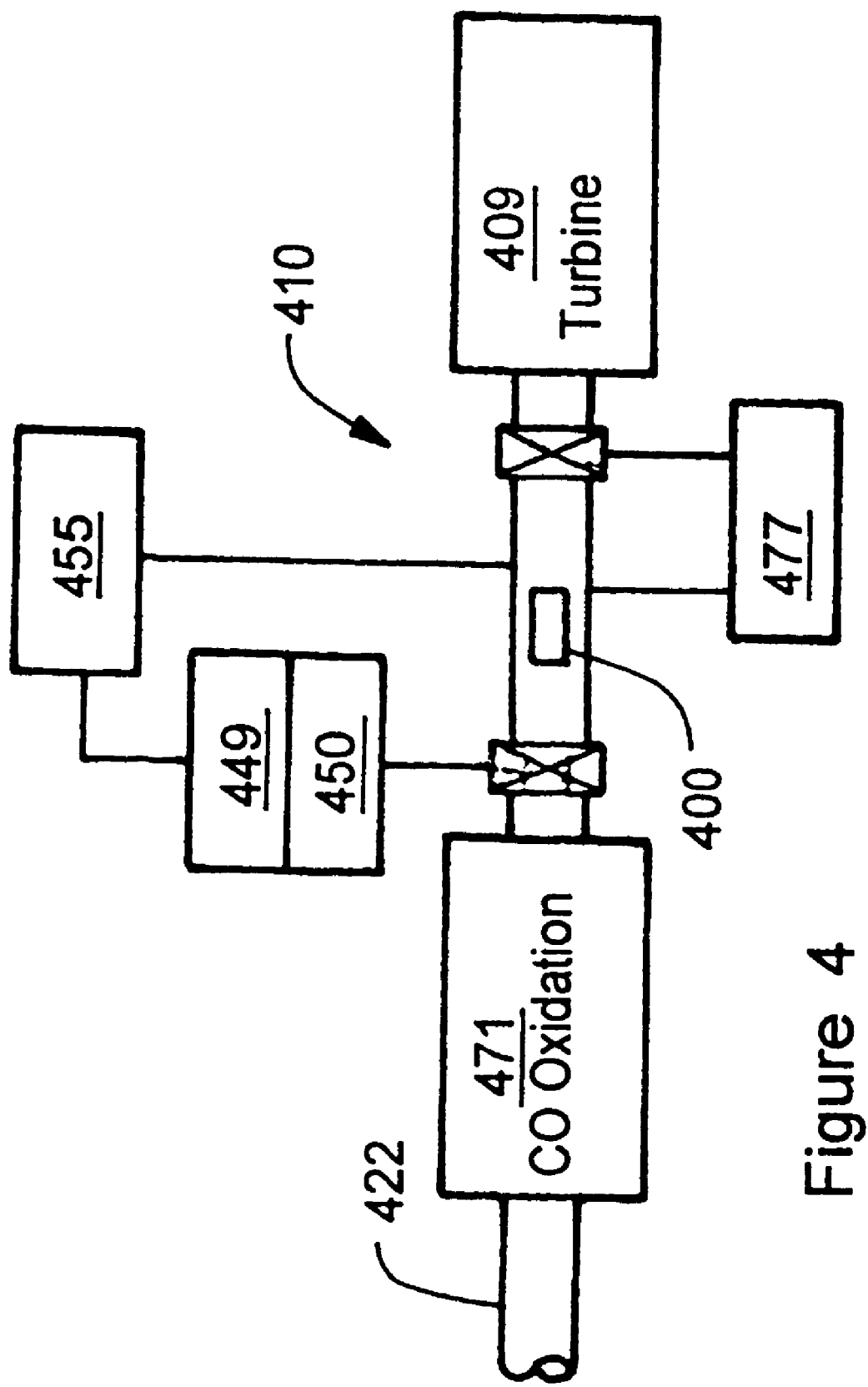
FIG. 4 is a top view cut away of a reducing catalytic means to remove CO from a hydrogen rich stream.

FIG. 4 depicts a simplified schematic of a CODAP system 410 of this invention including the CO-to-methane catalyst system 477 and a sensor control system 455 as a part of fuel conditioning systems 471 and 477 and in-line CO sensor 400 which is a part of the fuel cell reformer system. The hydrogen rich stream leaves the CO Oxidizer 471, and the CO concentration may be measured both before (not shown) and after the oxidizer 471 by a catalytic sensor 400 that measures by means of a temperature differential between a control sensor and a catalytic sensor. An optional CO sensor chamber or unit 455 is incorporated in a side stream, which side stream passes through a cooling means 450 before entering the sensing chamber 455. The cooling means 450 lowers the temperature of the gas stream, and a membrane 499 is used to remove condensed water exiting from the cooling means 450 before entering the sensor chamber 455.

The CO catalytic converter 477 reduces the CO to methane gas. It may be used all the time or as needed or in an emergency depending on the measured CO level.

FIG. 5 is a cut-away perspective view of one of the filter elements 510 in a catalyst system 577. The catalyst 571 is made of nickel coated onto a porous high-surface area solid substrate such as aluminum oxide (not shown). The gas stream comprises CO 572 and hydrogen 573 and other gasses 574, including carbon dioxide. The gases pass through a first perforated plate 576 adjacent the catalyst inlet, then though the catalyst bed 571 where the CO is reduced to methane in the presence of hydrogen. The reaction products finally leave the catalyst via a porous outlet plate 576. Heat is provide by combustion or waste heat to promote efficient reduction.

FIG. 6 depicts a remotely operated fuel cell reformer system 610 comprising a reformer 670 that is positioned some distance away from a fuel cell 675, and a transmission line 666 to carry the fuel (not shown) from the reformer to the fuel cell, e.g., under the water 699 to the light house 602. There may be control signals sent by wire or by radio signal to the two different locations, and there may be several fuels cells that operate on one central reformer.

FIG. 7 is a schematic of CODAP system 710 of this invention as used in part of an ammonia synthesis plant 700. A hydrogen rich stream passes by a sensor 777, which comprises a thermal sensing system, explained in more detail below and illustrated in FIG. 10, and may also comprise a biomimetic sensor system 755. The CO and other sensor inputs are used to control the fuel systems by means of a controller or control system 760. CO may be removed from the hydrogen stream by a catalytic converter 777, which converts the CO to methane. A nitrogen stream reacts with the purified hydrogen stream over a catalyst system (not shown) at high temperature and pressure in a reactor 703. Ammonia exits the reactor 703 where it may be separated from the methane upon liquefaction of the ammonia (not shown).

FIG. 8 illustrates a schematic of a hydrogen generation and bottling system 810 comprising a reformer 870 and at least one sensor system to monitor CO with a CODAP system 851 of this invention. Hydrogen is generated from a hydrocarbon such a DF-2 (not shown), and a hydrogen rich stream is sampled through a CO sensing chamber 855, before bottling the hydrogen in the bottle 806 after passing through a catalytic means 877 to remove CO and a valve/regulator system 807. The CO sensor(s) not shown in 855 provide input to the control 860, which can control the process to keep the CO below a predetermined level or shut down the system when necessary.

Figure 9:
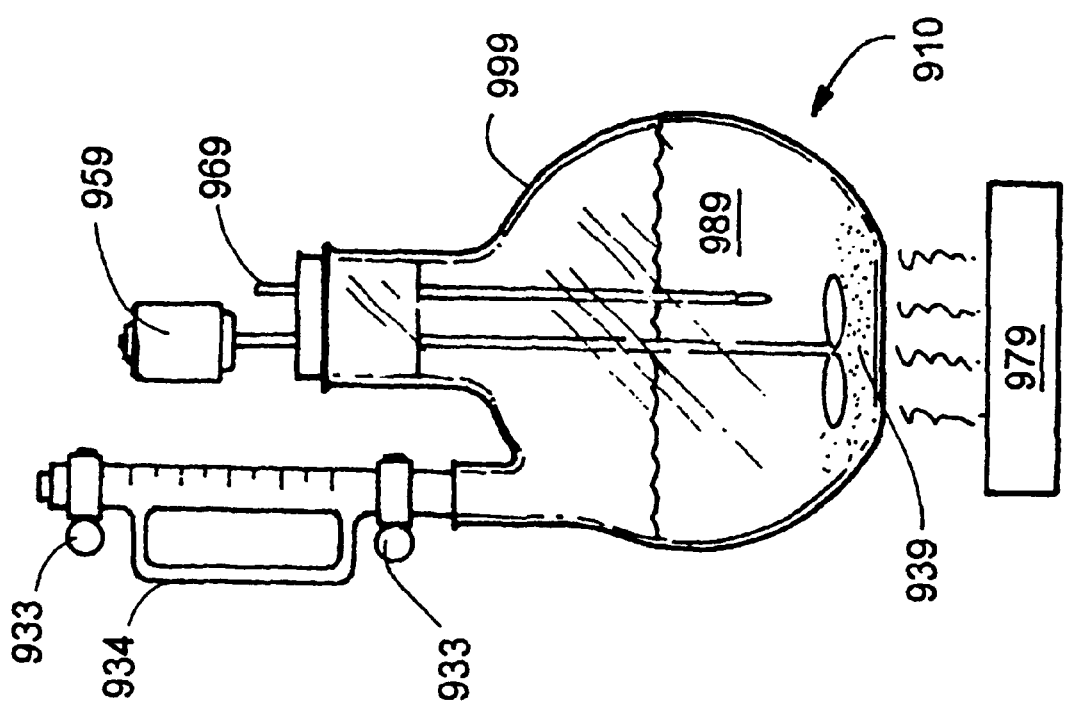
FIG. 9 schematically illustrates a method for producing high-surface-area nickel on the surface of a substrate which is coated onto a thermal sensing element.

FIG. 9 illustrates a method to manufacture a catalyst 910 useful for converting CO to methane. The same method may be used to make a catalytic CO sensor when it is applied to the thermal sensor and a control chemical with a very similar thermal conductivity is applied to a control thermal sensor by a very similar means as illustrated in FIG. 10. Referring to FIG. 9, substrates 939 such as alumina or silica can be prepared by a method to make porous materials with high surface areas and controlled pore sizes such as by the sol-gel method. The activated substrate 939 is coated with high surface area sodium dispersion 989. The high surface area substrate coated with sodium is next reacted with a metal chloride 934 that is soluble in the organic solvent. The solvent is selected such that it will dissolve the metal chloride 934 or a metal chloride complex and precipitate the insoluble sodium chloride (not shown). The mixture is located in a reaction vessel 999 that may be heated or cooled by a means 979. The temperature may be monitored by a thermometer 969. The metal chloride such as nickel chloride or organometallic nickel chloride complex is added drop wise by controlling two stopcocks 933 at the top and bottom of the dispenser containing the metal chloride 934.

A thin coating of the metal catalyst (not shown) such as monomolecular nickel acts as the catalyst to sense and or convert CO to methane in the presence of excess hydrogen.

FIG. 10 illustrates a differential thermal sensing means for CO a the gas stream. The thermal sensing means comprises a thermal sensing element 1004 that is located at a center of a CO sensor 1000. The CO sensor 1000 is first coated with a catalyst system 1080, which comprises a high surface area ceramic oxide 1012 such as silica or alumina. This coating is accomplished by using one of several methods.

One example method is by dip coating an alkoxide which dries to form a porous solid that is bonded to a thermistor or other thermal sensor 1004. Another example method is to first convert the aluminum alkoxide into a stable organometallic acid (not shown) such as by reacting the metal oxide with a complexing agent to give a mixture of complexing agent-alkoxide metal complex, hydrolyzing said complexes and isolating the metal oxide ceramic precursor, mixing it with a solvent, and costing the metal oxide by dip or spray methods.

Next to a catalytic sensor 1020 is a control thermal sensor 1030. The control sensor 1030 is coated with a noncatalytic metal on an oxide 1040. The metal oxide 1040 is coated with an alloy 1022 that has the same thermal conductivity as the catalytic material used to form the control sensor 1020. The control thermal element 1030 is coated with a metal oxide 1040 such as alumina or silica, which in turn is coated with a metal or mixture of metals such as copper, gold silver or alloys such that the thermal conductivity is the same as the CO sensor 1000. Thus, in a zero CO concentration there is no differential signal in the temperature range of operation (180° C. to 300° C.).

Figure 11:
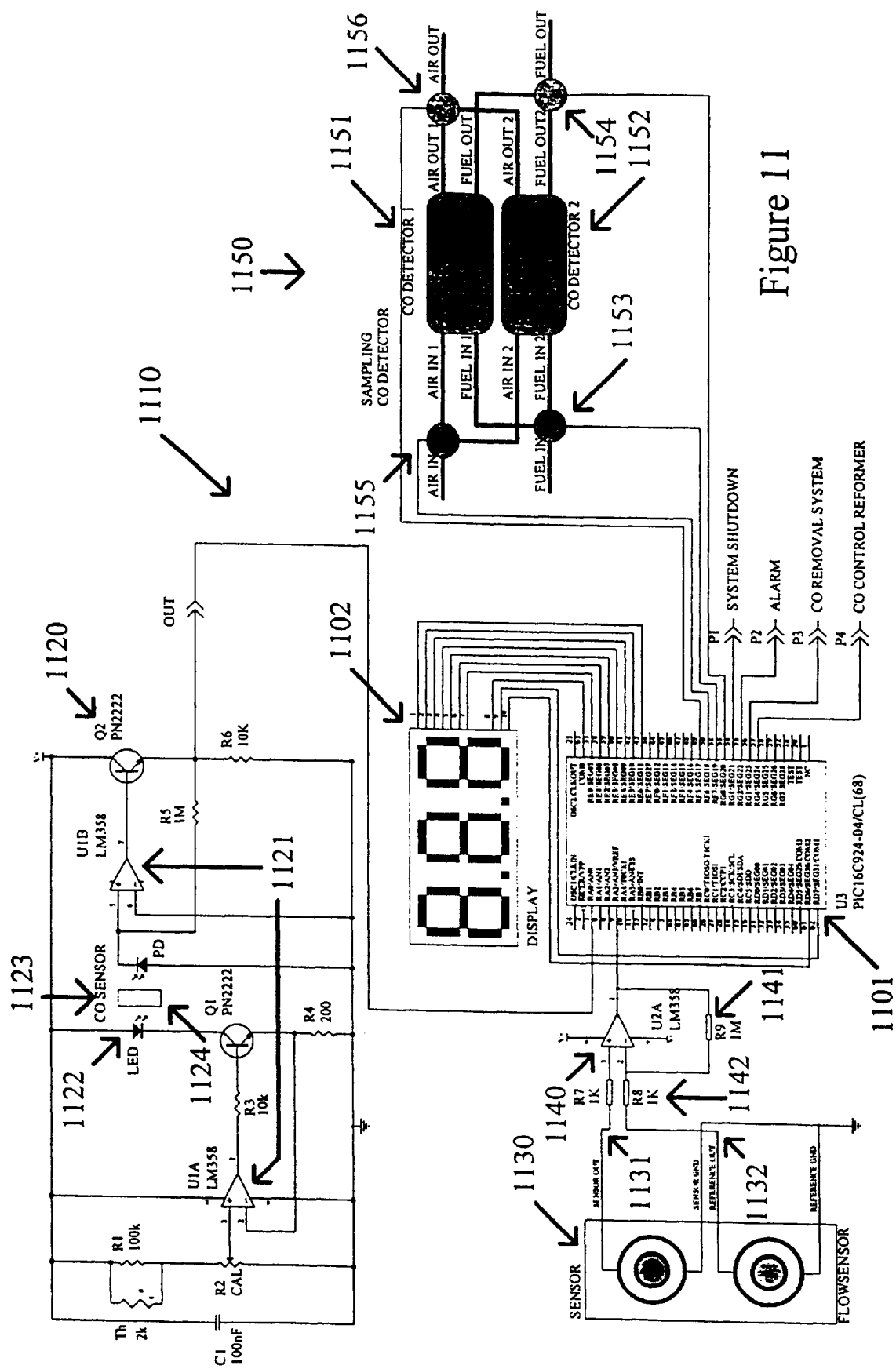
FIG. 11 schematically illustrates means for controlling the biomimetic sensing system and for providing information to control the fuel cell reformer process.
Figure 12:
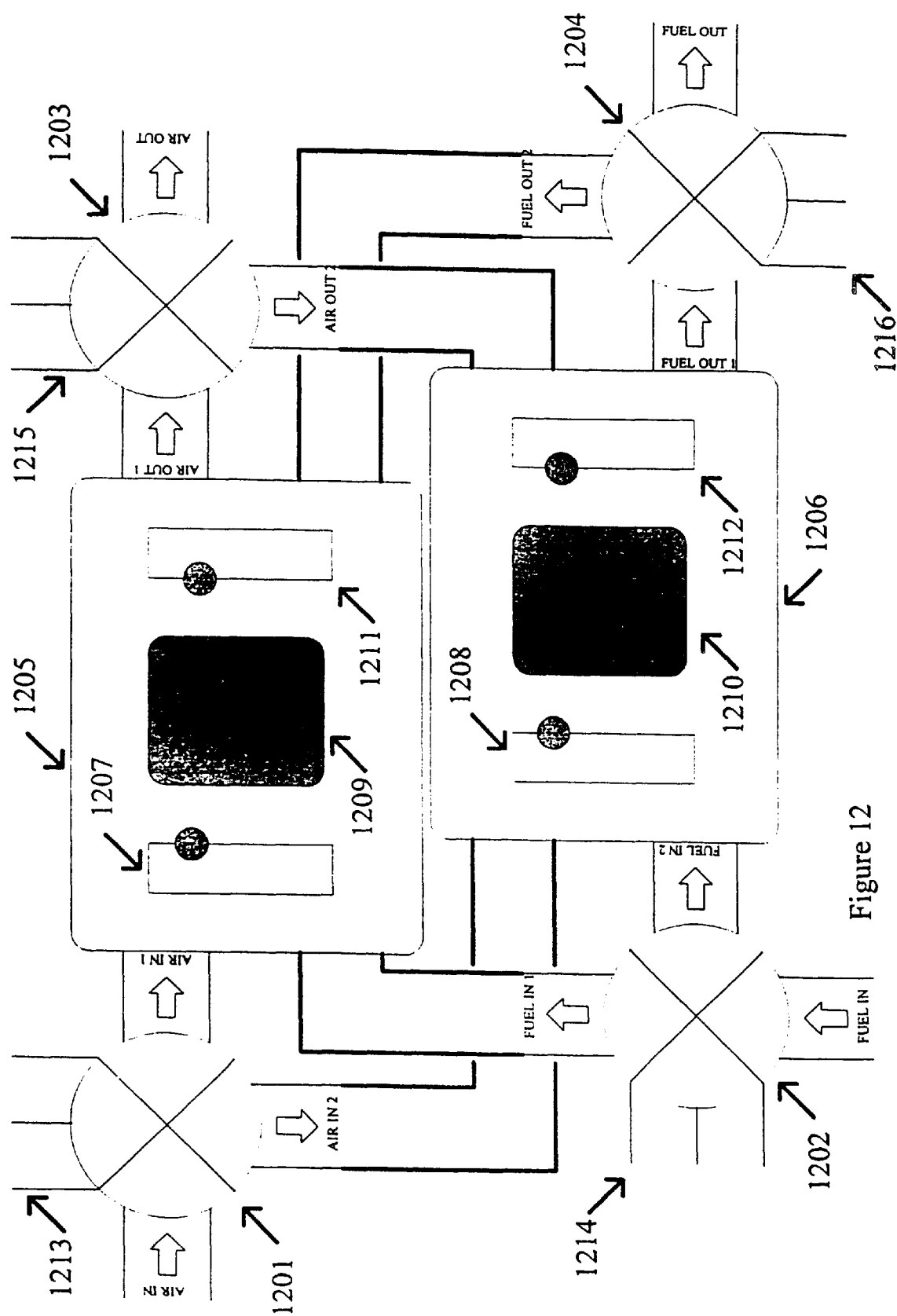
FIG. 12 schematically illustrates a control means for measuring the differential conductivity of a nickel catalyst coated onto a high surface area substrate coated onto a ceramic thermistor, and providing feedback to control the fuel cell reformer system.

At normal operating conditions, in the gas stream leaving the selective oxidizer described above, there are small amounts of CO (1–10 ppm), if something goes wrong it can changed to another range such as from 11 to 1000 ppm and more. The speed of the sensor system reaction is therefore important to correct the problem quickly. By coating with a relatively thin coating such as 2–10 microns, sufficient reaction speed can be assured. The smallest coating is a monomolecular layer is only a few angstroms. The CO sensor 1000 and the control sensor 1020 are connected in a circuit designed to measure the differential signal as described below and illustrated in FIG. 11. The signal from the sensor system of FIG. 10 is calibrated such that a digital CO output is feasible. The details of this control means and circuit are described better below and are illustrated in FIGS. 11 and 12 below.

The CO Detection and regeneration system comprises a dual CO sensor one of which is a control sensor to reduce effects of environmental changes such as temperature and relative humidity.

Another method can be used to coat thermistors, thermally sensitive elements and other materials with similar expansion coefficients with a porous metal oxide. If the coefficients of expansion vary greatly a series on intermediate coating may be used to grade the bonding. This may be accomplished by first making precursors of metal oxides. This method include both organic and inorganic methods. The use of metal nitrates that are dip or spray coated and then reduce to the hydroxide by reaction with ammonia. The hydroxide may then be dried and fired to produce a porous oxide. The pore size may be controlled by the adjustment of pH and concentration of the nitrate as well as the firing temperature. This method is described in U.S. Pat. No. 5,356,487, which is incorporated herein by reference.

Another important method useful for producing porous metal oxide coatings is to first prepare an organometallic precursor as described in U.S. Pat. No. 5,662,737, which is incorporated herein by reference. The following is a modification of the above patented process.

Add 600 g of 0.5 molar solution aluminum isopropanol or similar aluminum alkoxide under dry nitrogen; add drop wise a solution containing 40 grams of 2-ethylhexanic acid in 250 ml of isopropanol. After the reaction becomes milky add a solution containing 95 grams of isopropanol and 5 grams water. Reflux for 2.5 hours at 70° C. Cool to 0° C. with ice. Then remove at all solvent at room temperature by vacuum evaporation, which leaves the solid acid metal compound. A non-polar solvent (such as cyclohexane) is mixed with the powder to form a solution. A high surface area metal oxide can be form by dip coating in air and drying at 500° C. The surface area and thickness of the high surface area metal oxide depends on the amount of solvent and its viscosity. The firing temperature can also effect the properties. After firing the early stage sensing element is coated with high surface sodium using a dispersion of sodium in an organic solvent. The high surface sodium is getting in an inert atmosphere and the place in a solvent such as dimethoxyethane. Then add a 100 ml of 6 grams of nickel chloride (in an organic solvent such as DME and or alcohol) drop wise. The nickel replaces the sodium leaving the precipitate of sodium chloride, which is not soluble in the solvent. Thus a high surface area active catalyst is prepared.

Using the same basic method, but using porous activated aluminum oxide in place of the metal oxide forming step, i.e., applying the high surface area sodium directly to the activated alumia and proceed as above such that a 1 to 2 molecular layers are applied to the surface, based on the standard surface area calculations or those obtained from standard BET surface area measurements.

A method for making porous silica based substrates and monolithic structures for coatings use $TMOS=Si(OCH_3)_4$ and/or $TEOS=Si(OCH_2CH_3)_4$.

$nSi(OR)_4 + 4n$ water $= nSi(OH)_4 + 4n$ ROH where R is either methyl or ethyl groups. An acid or base catalyst may be used to increase the rate of reaction. Raising the temperature to 65° C. increase the rate and leads to bulk densities of about 1.0 to 1.2 g per cubic cm. HCl catalyst results in a clear gel with porous sizes about 10 to 25 angstroms. The use of basic catalyst, such an ammonium hydroxide, shrinks less than acid catalyst: however, in a thin coating shrinkage is less of a problem. This method is well known as is describe in a book by Edited by L. Klien entitled "Sol-Gel Technology for Thin Films, Fibers, Preforms, Electronics and Specialty Shapes" Noyes Publication 1988, Pages 50 to 99.

Another method is to produce a high surface area nickel directly on the thermal sensor. There are several methods that produce very porous or raining nickel.

Platinum substituted for palladium in the biomimetic supramolecular compounds may be used to provide a control. These control CO sensors do not react with the CO and therefore that does not respond photometrically to CO but does tract humidity, temperature and pressure.

This additional accuracy obtained by means of a control sensor allows accurate reliable sensing at levels as low as 5 to 10 ppm, in a low cost device without regular calibration. Thus this dual sensor system may be used to determine when the levels of CO should be addressed in a fuel cell such as a vehicle system where it is very important to reduce the CO concentration to prevent getting stuck on the highway.

The sensor is a material comprising palladium salts, copper salts, silicomolybdic acid combined with various other compound such as cyclodextrins to form a supramolecular complex which can be self assembled from a solution onto a high surface area substrates such as silica gel or other porous silica glasses.

An example of the chemistry that is used for the control sensor and the catalyst is described below: porous silica substrate with a weight of about 100 grams 75 mg palladium chloride 20 ml silicomolybdic acid (30 g/l)

25 ml copper chloride (200 g/l)

I molecular equivalent of beta cyclodextrin to palladium ions and 450 mg of calcium chloride The difference between the sensor and the control sensor is only the substitution of platinum for palladium on mole bases. The sensor is dried very slowly after the solution is applied to a disk shaped monolithic with the diameter about 5 mm and the thickness about 1 mm. This porous substrate is easily mounted for optical monitoring.

FIG. 11 illustrates an electronic control circuit 1110 for CO detection and monitoring systems of this invention. The control circuit 1110 includes a microprocessor U3 1101 that is configured to collect the CO concentration information from the sensor system. There are two detection circuits. A low linear range (LLR) circuit 1120 is designed having a dual operational amplifier U1 1121, and a light emitting diode LED 1122, a CO sensor 1123, and a photodiode PD 1124. High CO (HCO) concentration is detected by a flow sensor 1130 circuit signal, and amplified by an operational amplifier U2A 1140.

The LLR circuit works in conjunction with the sampling CO detector (SCOD) 1150. The SCOD has two sampling chambers, sampling chamber no. 1 1151, and sampling chamber no. 2 1152. The two sampling chambers work in opposition. Let us say that the fuel in valve 1153 allows the fuel sample to go into sampling chamber no. 1, and the fuel out valve 1154 lets the fuel sample be evacuated from sampling chamber no. 1. At the same time the air in valve 1155 allows the air to circulate in sampling chamber no. 2, and the air out valve 1156 allows the air to be evacuated from sampling chamber no. 2. At this point, the CO sensor mounted in sampling chamber no. 1 detects CO, and the CO sensor mounted in sampling chamber no. 2 is regenerating due to the fresh airflow. After a certain time, the role of the two sampling chambers is reversed when the air in, fuel in, air out and fuel out switch simultaneously from one chamber to the other. Now the chamber in which the sensor was regenerating will receive a sample of the fuel, and the chamber in which the sensor was exposed to the fuel sample will receive fresh air, in order to regenerate.

The microprocessor U3 1101 collects the analog voltage from the LLR circuit and makes the analog to digital conversion, storing the CO concentration information in a dedicated 8-bit register. If the CO concentration exceeds a preset value, the CO removal system is activated in order to reduce the amount of CO in the fuel flow.

A digital display 1102 is provided for the immediate CO concentration monitoring. The microprocessor employed in the schematic has a built in LCD driver. The many other features of this state of the art microprocessor allows the implementation of many other functions of the system, such as digital and/or analog inputs, serial data/Pulse Width Modulation/digital outputs, flash memory EEPROM data exchange and storage, and more.

A CO flow sensor 1130 was employed for the high level range CO (HLR) concentrations. See the description for FIG. 10. Due to the nature of this sensor, a differential amplifier circuit was used. The sensor has two active outputs. One output delivers an analog output proportional with the CO concentration (sensor out) 1131, and the other output (reference out) 1132 provides the temperature compensation for the active signal. A differential operational amplifier 1140 receives the active CO analog voltage on the non-inverting input and the reference voltage, due to the temperature variation, on the inverting input. Adjusting the ratio between a feedback resistor (R9) 1141 and an input resistor (R8) 1142 sets the gain of the circuit.

The final output voltage of the differential circuit excludes the temperature effect:

$$V_{OUT} = [(V_{CO} \, q - V_{TEMP/CO}) - V_{TEMP/REF}] \times GAIN$$

Where:
$V_{OUT}$ is the output voltage of the operational amplifier
$V_{CO}$ is the CO sensor voltage output due to CO
$V_{TEMP/CO}$ is the unwanted voltage drift due to temperature of the CO sensor
$V_{TEMP/REF}$ is the output voltage of the temperature compensation element GAIN is the ratio R9/R8.
If $$V_{TEMP/CO} = V_{TEMP/REF}$$

then $$V_{OUT} = [(V_{CO} + V_{TEMP/CO}) - V_{TEMP/REF} \times] GAIN = V_{CO} \times GAIN$$

The HLR circuit voltage output is converted into a digital value and stored in a dedicated 8-bit register.

This value is used to trigger different events, according to the logic employed by the system designer. The high-level range CO can trigger alarms, or even the system shut-off.

The electronic control circuit can be implemented in many different ways, and is not reduced to the components shown in FIG. 11. A programmable logic device can also replace the microprocessor; the analog to digital converter can be a distinct component, not included in the microprocessor.

The active sensor output 1131 is connected in a circuit with a control sensor output 1132. At the center of the two circles in the box marked sensor 1130 is the thermistors. One method to prepare the active sensor is to coat (dip or spray) a ceramic thermistor element with a porous metal oxide by one of the methods described above or the other method described above and illustrated in FIG. 10.

The porous metal oxide may be from 1 to 30 microns. After drying and heating the high surface area metal oxides, such as aluminum oxide, silicon oxide, titanium oxide, and mixture thereof, a very thin layer of nickel or other catalytic metal is deposited on its surface. It is preferred to deposit a 1 molecular layer. However, in practice, a 10 to 30% excess may be required to get complete surface coverage. The nickel may be coated by vacuum method or by first applying sodium to the surface and then replacing it in an organic solution in which sodium chloride is very insoluble as discussed above.

FIG. 12 shows in greater detail the sampling CO detector, the gas paths, and the control pins. The CO sensors 1209 and 1210 are placed in the respective sampling chambers 1205 and 1206, between the respective LEDs 1207 and 1208 and the respective photodiodes 1211 and 1212. Airflow to the respective sensor chambers is provided by an air in valve 1201, and is removed by an air out valve 1203. A sample fuel stream is provided to te respective sensor chambers by a fuel in valve 1202, and is removed from the sensor chambers by a fuel out valve 1204. The succession in which the four valves are operated is established by the microprocessor's software and follows the logic described above for the embodiment illustrated in FIG. 11. All valves are actuated by signals applied at the control pins 1213, 1214, 1215 and 1216.

Those skilled in the art would readily appreciate that the scope of the invention is not limited to the presently preferred embodiment. For example, any number of properties of the sensor may be measured such as, for example, reflection of light from the sensor(s), conductivity, impedance, temperature and others.

Also, one of ordinary skill in the art would recognize that any one of a variety of microprocessors and other circuit elements could be used to implement the invention, including those with built in analog to digital converters, built in liquid crystal display drivers.

One skilled in the art would appreciate an apparatus and method for digitally tracking the response of optically responding sensors for a variety of target gases. Such an apparatus and method would increase the desirability of a wide variety of products from home detectors to personnel monitors to industrial control to automotive.

Many other modifications and variations will be apparent to those skilled in the art, and it is therefore, to be understood that within the scope of the appended claims the invention may be practiced otherwise than as specifically described. Because the current products on the market that are battery operated use electrochemical cells for sensors they are very expensive, require frequent calibration, and frequent replacement, other products use Metal Oxide Semiconductor sensors which take very large amounts of power and therefore can not be operated practically on small batteries. Therefore there is a need for a low cost, reliable, accurate, easy to use battery powered unit to detect CO level, TWA, Dose, as well as rate of change of the CO.

We claim:

1. A method for determining the concentration of carbon monoxide within a hydrogen rich stream of a fuel cell reformer comprising the steps of:

passing a portion of the hydrogen rich stream into a first sensor chamber that includes at least one sensor that is responsive to carbon monoxide;

exposing at least one sensor that is responsive to carbon monoxide, and that is disposed within a second sensor chamber, to air to regenerate the same;

determining the level of carbon monoxide present in the hydrogen rich stream by monitoring the response of the sensor exposed to thereto; and routing the hydrogen rich stream to the second sensor chamber, and exposing the sensor within the first sensor chamber to air, when a predetermined carbon monoxide saturation level is satisfied.

2. The method as recited in claim 1 further comprising the step of displaying the level of carbon monoxide detected by the sensor exposed to the hydrogen rich stream on a display device.

3. The method as recited in claim 1 further comprising the step of reducing the temperature of the hydrogen rich stream before it is routed to the first or second sensor chamber.

4. The method as recited in claim 1 wherein the first and second sensor chambers each comprise a sensor that is optically responsive to carbon monoxide, a photon source for emitting photons onto the sensor, and a photodetector for receiving photons emitted onto the sensor, wherein the step of determining the level of carbon monoxide comprises intermittently measuring the optical characteristics of the sensor exposed to the hydrogen rich stream, and wherein the method further comprises the step of providing an alarm signal when the level of carbon monoxide exceeds a predetermined set point.

5. The method as recited in claim 1 further comprising the step of taking a differential measurement from a control sensor and a catalytic sensor, wherein the control sensor and the catalytic sensor are equally responsive in an air environment in the absence of carbon monoxide.

6. The method as recited in claim 5 wherein the catalytic sensor comprises a nickel catalyst and sensor properties that are measured to determined carbon monoxide level are selected from the group consisting of resistance, conduction, impedance, temperature, voltage, amperes, watts, and combinations thereof.

7. The method as recited in claim 1 wherein at least one of the sensor chambers comprises a set of sensors that are optically responsive to carbon monoxide at increasing threshold and decreasing sensitivity, and wherein the step of determining the carbon monoxide level comprises converting a sensor photometric response of an exponential response curve to a digital signal by solving an exponential equation of the carbon monoxide response curve.

8. The method as recited in claim 1 wherein the step of determining comprises the step of assigning a sensor reading value to a measured sensor optical characteristic, wherein the reading is proportional to an optical characteristic of the sensor.

9. The method as recited in claim 1 wherein the sensors disposed in each of the first and second sensor chambers is a biomimetic sensor comprising palladium, copper, molybdenum, calcium, cyclodextrins chlorides, bromides, and an acid.

10. The method as recited in claim 1 wherein the sensors comprise a porous silica substrate that is coated with a chemical reagent comprising at least one of the following groups:

Group 1—palladium salts selected from the group consisting of palladium sulfate, chloride, and bromide;

Group 2—heteropolymolybdates selected from the group consisting of silicomolybdic acid, ammonium molybdate, and alkali metal molybdatesl Group 3—copper salts of sulfate, chloride, bromide and perchlorate;

Group 4—alpha, beta, gamma or delta cyclodextrins and e hydroymethy ethyl and propyl derivatives thereof; and Group 5—soluble salts of alkaline and alkali chlorides and bromides.

11. The method as recited in claim 4 wherein the step of determining the level of carbon monoxide level comprises using a microcomputer to sum the entries of the table of differences, add the summed entries in an alarm register; and enter an alarm mode or control mode when the alarm register exceeds a predetermined activation point.

12. The method as recited in claim 11 wherein the step of entering the alarm or control mode comprises entering one of a plurality of activation modes proportional to the determined CO levels, and further comprising the use of a control sensor, a circuit, and an optical comparison means to measure a difference between the sensors disposed in the first and second sensor chambers and the control sensor.

13. The method as recited in claim 11 further comprising the step of increasing the rate of intermittent readings upon entry into one or more of the activation modes.

14. The method as recited in claim 11 wherein the step of adding the summed entries in the control activation register ceases when the control activation register exceeds the predetermined action level.

15. The method as recited in claim 1 wherein the step of determining comprises differentiating a plurality of sensor optical transmittance values with respect to time and measuring the optical transmission, and using the measured values to compute the carbon monoxide concentration, further comprising the step of using a Taylor series to approximate the exponential form of the sensor response.

16. The method as recited in claim 1 wherein the step of determining comprises making a plurality of initial optical transmission readings of the sensor chamber exposed to the hydrogen rich stream;

making a plurality of subsequent readings of the same sensor, each subsequent reading being made a predetermined time after an adjacent initial reading; and subtracting the initial readings from adjacent subsequent readings to produce a plurality of differences and using the values of the optical state of the sensor and its rate of change deviate to determine the carbon monoxide concentration and to evaluate whether a desired control action is necessary.

17. The method as recited in claim 1 further comprising the step of passing the hydrogen rich stream through a means for reducing carbon monoxide levels when a predetermined carbon monoxide level is detected.

18. An apparatus for detecting and measuring the level of a target gas within a hydrogen rich stream of a fuel cell reformer comprising:

a first sensor chamber that includes at least one sensor that is responsive to the target gas, the first sensor chamber being in communication with the hydrogen rich stream and a fresh air stream;

a second sensor chamber that includes at least one sensor that is responsive to the target gas, the second sensor chamber being in communication with the hydrogen rich stream and a fresh air stream;

means for selectively exposing the first and second sensor chambers to one of the hydrogen rich stream and the fresh air stream; and means for controlling the means for selectively exposing so that the hydrogen rich stream is switched off and fresh air is directed to the first or second sensor chamber that comprises a sensor operating at a predetermined saturation level, and wherein the means for controlling directs the hydrogen rich stream to the other of the first or second sensor chamber previously exposed to fresh air.

19. An apparatus as recited in claim 18 wherein the target gas is carbon monoxide, the sensors are optically responsive to the target gas, and each of the sensor chambers include a photon emitting source and a photon receiving source.

20. An apparatus as recited in claim 19 further comprising means for determining the carbon monoxide level within the hydrogen rich stream from optical transmission information provided from the sensor chambers.

21. An apparatus as recited in claim 20 further comprising means for providing an output signal when the determined carbon monoxide level reaches a predetermined set point.

22. An apparatus as recited in claim 18 wherein the means for selectively exposing comprises one or more valves within the hydrogen rich stream to control passage of the stream to one of the first and second sensor chamber, and comprises one or more valves within a fresh air stream to control the passage of fresh air to the other of the first and second sensor chamber.

23. An apparatus as recited in claim 19 wherein the sensors comprise a porous silica substrate that is coated with a chemical reagent comprising at least one of the following groups:

Group 1—palladium salts selected from the group consisting of palladium sulfate, chloride, and bromide;

Group 2—heteropolymolybdates selected from the group consisting of silicomolybdic acid, ammonium molybdate, and alkali metal molybdatesl Group 3—copper salts of sulfate, chloride, bromide and perchlorate;

Group 4—alpha, beta, gamma or delta cyclodextrins and e hydroymethy ethyl and propyl derivatives thereof; and Group 5—soluble salts of alkaline and alkali chlorides and bromides.

24. An apparatus as recited in claim 18 further comprising means for reducing the level of the target gas in the hydrogen rich stream when the target gas level is above a preset amount.

25. An apparatus as recited in claim 24 wherein the means for reducing comprises a metal catalyst selected to convert the target gas to a hydrocarbon fuel.

26. An apparatus as recited in claim 18 wherein the apparatus is installed between a reformer and the fuel cell.

27. An apparatus as recited in claim 18 further comprising means for cooling the hydrogen rich stream before reaching one of the first or second sensor chambers.

28. An apparatus as recited in claim 27 further comprising means for removing water from the hydrogen rich stream leaving the cooling means before reaching one of the first or second sensor chambers.

29. An apparatus as recited in claim 19 further comprising another sensor disposed in hydrogen rich stream that is thermally reactive to the target gas.

* * * * *

UNITED STATES PATENT AND TRADEMARK OFFICE
CERTIFICATE OF CORRECTION

PATENT NO.     : 6,429,019 B1
DATED          : August 6, 2002
INVENTOR(S)    : Mark K. Goldstein et al.

It is certified that error appears in the above-identified patent and that said Letters Patent is hereby corrected as shown below:

<u>Title page, Item [54] and Column 1, line 2,</u>
Title, replace "FUELS" with -- FUEL --.

Signed and Sealed this

Twenty-sixth Day of August, 2003

JAMES E. ROGAN
*Director of the United States Patent and Trademark Office*